Figure 1:
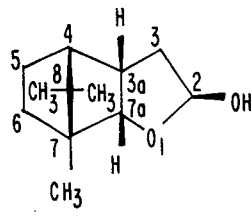

United States Patent [19]

Noe

[11] Patent Number: 4,497,960
[45] Date of Patent: Feb. 5, 1985

[54] CHIRAL, OPTICALLY ACTIVE COMPOUNDS USEFUL AS PROTECTIVE GROUPS FOR HYDROXY, THIOL AND AMINO COMPOUNDS

[76] Inventor: Christian Noe, Larochegasse 20/7, A-1130 Vienna, Austria

[21] Appl. No.: 446,944

[22] Filed: Dec. 6, 1982

[30] Foreign Application Priority Data

Dec. 18, 1981 [AT] Austria ............................. 5453/81

[51] Int. Cl.$^3$ .................. C07D 311/94; C07D 307/93
[52] U.S. Cl. .................................... 549/386; 549/459; 260/453.7; 560/60; 560/147; 568/324; 568/67; 568/810; 568/808; 562/512; 564/303; 564/304
[58] Field of Search .............................. 549/459, 386

[56] References Cited

U.S. PATENT DOCUMENTS 4,159,258 6/1979 Ohloff et al. .................... 549/386
4,438,023 3/1984 Skorianetz et al. .............. 549/386

FOREIGN PATENT DOCUMENTS 2826302 1/1979 Fed. Rep. of Germany .

OTHER PUBLICATIONS

Hertli et al., Helv. Chim. Acta, 64, 25 (1981).
Miller et al., Tetrahedron Lett., 37, 3347 (1974).

Primary Examiner—Nicky Chan
Attorney, Agent, or Firm—Marshall, O'Toole, Gerstein, Murray & Bicknell

[57] ABSTRACT

The invention declares new chiral, optically active compounds of the general formula

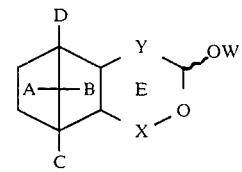

(I)

wherein a 5 or 6 membered lactol ring (E), with X and Y meaning $(CR^1R^2)_n$, with $n=0$ to 2 and $R^1$, $R^2=H$, lower alkyl or aryl in any combination which does not impair the anomeric selectivity of I in forming acetals, is fused in a stereospecific manner to a bicyclo[2.2.1]heptane ring system, with A,B,C,D meaning H or methyl in any combination, preferably a bornan ring system, and wherein W has the meaning of H, substituted or unsubstituted alkyl or cycloalkyl or the ring system itself, preferably H, and lower alkyl; and in the case of $W=H$ its anhydro compound of the general formula

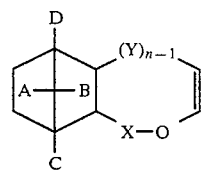

(V)

with A,B,C,D,X,Y and n having the same meaning as in the hydrated form, processes for their preparation and use of these new compounds for the protection of —OH, —SH, —NH— functions, for racemic resolution, for the preparation of optically active imidoester chlorohydrates as well as of optically active esters, for the preparation of optically enriched alcohols and for the preparation of optically active compounds via asymmetric induction.

12 Claims, 10 Drawing Figures

CHIRAL, OPTICALLY ACTIVE COMPOUNDS USEFUL AS PROTECTIVE GROUPS FOR HYDROXY, THIOL AND AMINO COMPOUNDS

Chiral, optically active compounds, processes for their preparation and use of these compounds for the protection of —OH, —SH, —NH— functions, for racemate resolution, for the preparation of optically active imidoester chlorohydrates as well as of optically active esters, for the preparation of optically enriched alcohols and for the preparation of optically active compounds via asymmetric induction.

The subject of the invention are new chiral, optically active compounds of the general formula I

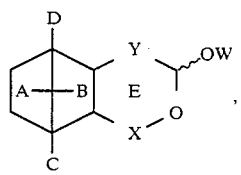
(I)

wherein a 5 or 6 membered lactol ring (E), with X and Y meaning $(CR^1R^2)_n$, with $n=0$ to 2 and $R^1, R^2 =$ H, lower alkyl or aryl in any combination which does not impair the anomeric selectivity of I in forming acetals, is fused in a stereospecific manner to a bicyclo[2.2.1]heptane ring system, with A,B,C,D, meaning H or methyl in any combination, preferably a bornan ring system, and wherein W has the meaning of H, substituted or unsubstituted alkyl or cycloalkyl or the ring system itself, preferably H and lower alkyl; and in the case of W=H its anhydro compound of the general formula

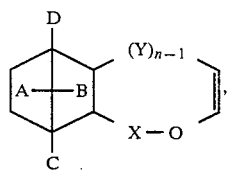
(V)

with A,B,C,D,X,Y and n, having the same meaning as in the hydrated compound, as well as processes for their preparation and the use of these new compounds for the protection of —OH, —SH, —NH— functions, for the resolution of racemates, for the preparation of optically active imidoester chlorohydrates as well as optically active esters, for the preparation of optically enriched alcohols and for the preparation of optically active compounds via asymmetric induction.

Compounds preferred according to the invention are chiral, optically active compounds ((R-enantiomer or (S)-enantiomer respectively) of the general formula

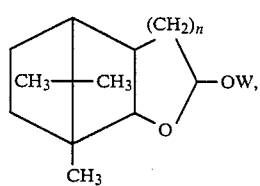
(Ia)

wherein W and n have the indicated meaning, and if W=H, the respective anhydro compounds of the general formula

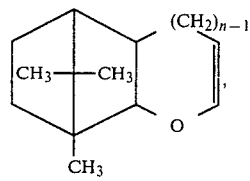
(Va)

wherein n has the same meaning as in the hydrated form.

Particularly preferred compounds according to the invention are chiral, optically active (R)-enantiomers and (S)-enantiomers of the general formula

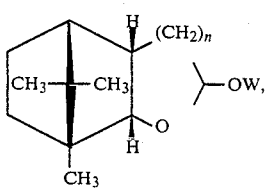
(Ib)

wherein W represents H, substituted or unsubstituted alkyl or cycloalkyl or the ring system itself and $n=0$ to 2 and, when W=H, the anhydro compounds of the general formula

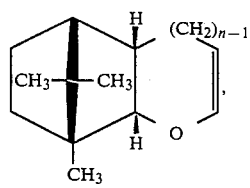
(Vb)

with n having the same meaning as in the hydrated form of formula Ib.

Tetrahydropyranyl and many other known acetalic protective groups have the disadvantage of causing the formation of diastereomers when reacting with chiral compounds and, in consequence, cause difficulties in isolating the products and performing further reactions.

The new chiral, optically active compounds declared in this invention are structured in such a way that they react in many cases with high anomeric selectivity with alcohols, cyanohydrins, thiols, amines, etc.

Besides their function as protective groups the anomeric selectivity prevents the formation of diastereomers in reactions with pure enantiomers. In reaction with racemic mixtures a pair of diastereomers is formed, creating favourable conditions for a resolution of the racemates through the separation of the diastereomers. In reaction with prochiral compounds, compounds of the general formula III are formed, which offer favourable conditions for reactions with asymmetric induction.

The essential reaction for the use of the new compounds according to this invention is shown in the following scheme 1:

Scheme 1

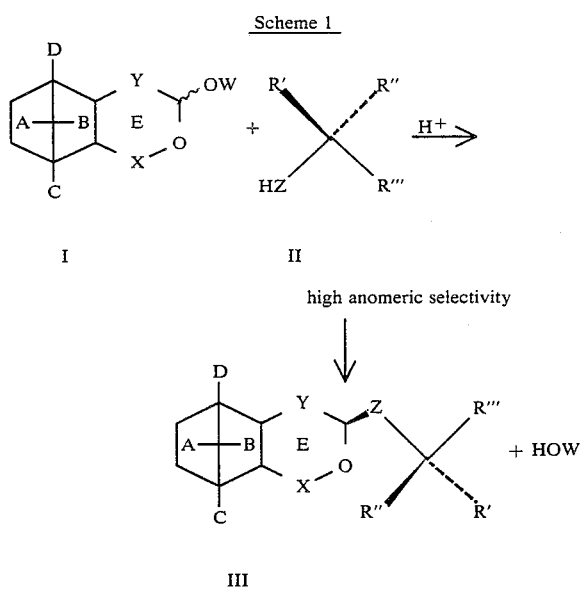

high anomeric selectivity

The general formula I indicates the optically active educt, which is—not taking into account the rest OW—a pure enantiomer reacting with compounds of the general formula II, where by in the educt, shown in formula I, a 5 or 6 membered lactol ring, with X and Y meaning $(CR^1R^2)_n$, with $n=0$ to 2 and $R^1, R^2 = H$, lower alkyl or aryl in any combination which does not impair the anomeric selectivity of I in forming acetals, is fused in a stereospecific manner to a bicyclo[2.2.1]heptane ring system, with A,B,C,D meaning H or methyl in any combination, preferably a bornan ring system (readily accessible from D(+) or L(−)-camphor), and wherein W has the meaning of H, as well as the meanings indicated below.

The original configuration of the rest OW in general formula I is of no importance, since formation of acetals proceeds via a carbonium ion of the general formula IV (scheme 2). Therefore substituent W is of minor importance too.

Scheme 2

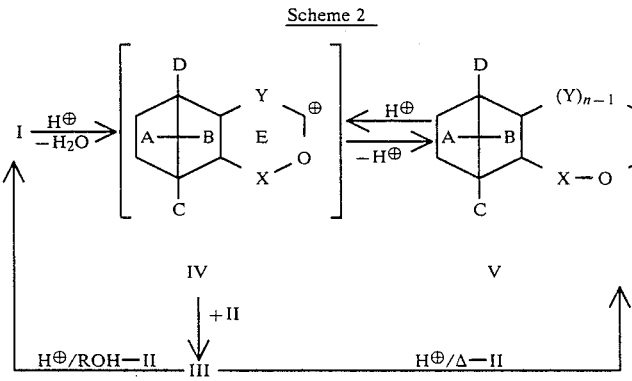

For the same reason the two dehydrated forms described below are compounds in the sense of the invention: there are the compounds according to formula I where W means the ring system itself (formally: lactol—½H₂O), which are formed by self-condensation of the lactol under the catalytic action of acids, and also the enolether according to formula V (formally: lactol—H₂O), which originates from the lactol under the influence of dehydrating agents or from compounds of the general formula III (Z=O) during vacuum distillation in presence of traces of acids through cleaving of the compounds of the general formula II.

As compounds of the general formula III may with advantage in some cases be prepared by transacetalisation—proceeding also via the carbonium ion according to formula IV—W also means substituted or unsubstituted alkyl or cycloalkyl, preferably a lower alkyl.

Optically active compounds of the general formula I (W=H) can easily be prepared by reduction from the corresponding lactones of the general formula VI, using preferably hydride reagents.

Scheme 3

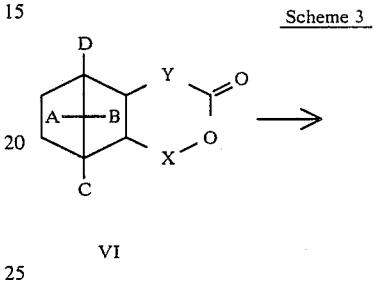

Compounds of general formula I (W=H) can be transformed into the self-condensed compounds of formula I (W=ring system itself) by treatment with catalytic amounts of a strong acid in inert solvents, into the enolether of the general formula V by the action of dehydrating agents, preferably inorganic acid choride/base and into the acetals of general formula I (W=substituted or unsubstituted alkyl or cycloalkyl, preferably a lower alkyl), which represent protective group reagents especially suited for repeated acetalisation processes, by treatment with catalytic amounts of strong acids in the presence of acyclic or cyclic alcohol, preferably lower alcohol.

Further processes for the preparation of optically active compounds of the general formula I are the selective reduction followed by cyclization of oxacid derivatives, the partial oxidation of diols, the addition of water to enol ethers of the general formula V, the photochemical ring expansion of condensed cyclobutanones, as well as cyclo addition reactions. Another method of preparing optically active compounds of the general formula I is the resolution of racemic compounds of the general formula I, especially suited are the racemic forms of the readily available norbornan derivatives of the general formula I (A,B,C,D=H). (Racemic educts of the general formula I (A,B,C,D=H) see: R. D. Miller, D. L. Dolce, V. Y. Merrit, Tetrahedron Lett. 1974 (37), 3347–50; G. B. Ohloff, W. D. Skorianetz, Ger. Offen. 28 26 302, 15.6.1978; L. Hertli and T. A. Kaden, Helv. Chim. Acta 64, 25–32, 1981.)

Compounds of the general formula V are also readily accessible via cyclo addition reactions.

In the meaning of the invention formula II in the preceding scheme 1, indicates the compound to react with or to be protected by compound I. For the use of I as a protective group reagent the only prerequisite is, that there is a —OH, —NH— or —SH function in the compound of the general formula II (Z=O,S,NH), which shows sufficient reactivity to react with a compound of the general formula I. In the case of use for asymmetric induction a suited prochiral arrangement is necessary beyond that. In the case of use as a reagent for resolution of racemates a chiral centre as near as possible to the —OH, —NH— or —SH function is a prerequisite. The rests R', R" and R"' have the meaning of H and substituted or unsubstituted alkyl-, aryl-, heteroaryl-, carbonyl, or nitrile groups, which are either arranged independently or connected to each other by an arrangement following the conditions mentioned above. In acyl compounds CR'R" have also the meaning C=O. With preference rests R',R" and R"' mean H, alkyl, 1-hydroxyalkyl, 1-oxoalkyl, aryl, substituted aryl, aryloxycarbonyl, aminocarbonyl and nitrile in any combination which does not impair the reactivity of II with compounds I or V respectively. For cyclic structures R', R" preferably mean —(CR$^1$R$^2$)$_n$— with n=3–7, R$^1$,R$^2$=alkyl and aryl, as well as —o-aryl—(CR$^1$R$^2$)$_n$, with n=2–4, R$^1$,R$^2$=alkyl or aryl in any combination.

Compounds of the general formula III are prepared by reactions of compounds of the general formula I with compounds of the general formula II catalyzed by acids. (Compounds I (W=ring-system itself) do not react with amines under the conditions given in the experimental part.) In addition to the protection of functional groups in compounds of the general formula II, there is, in many cases, a potential for racemate resolution using the separation of diastereomeric compounds of the general formula III (preferably via column chromatography and crystallisation), if racemic compounds of the general formula II are used. After separation of the diastereomers and, if desired, after carrying through further reactions with the separated compounds of the general formula III, the protective group can be cleaved by acid catalysis (as dimer of the general formula I (W=ring system itself) or methyl acetal of the general formula I (W=methyl)) and a pure enantiomer of the general formula II is obtained (compare scheme 4).

Scheme 4

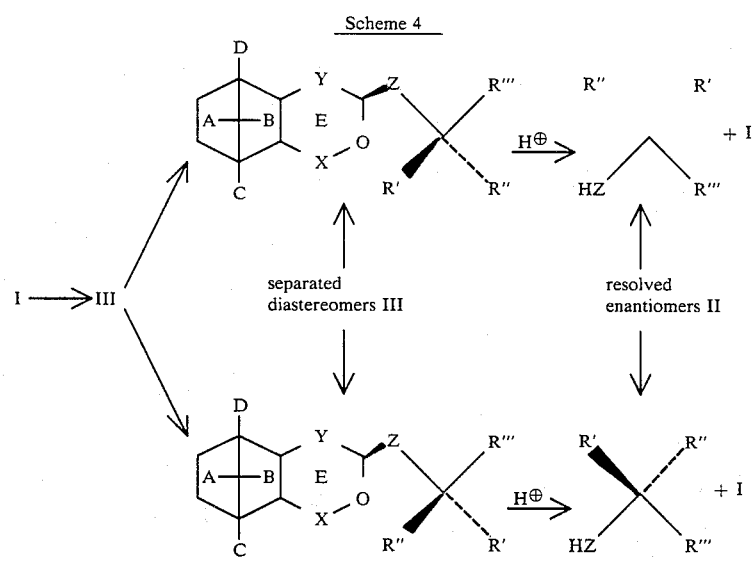

In the same manner resolved enantiomers of imidoester chlorohydrates can be obtained from protected cyanohydrins after separation of the diastereomers.

If acetals are formed from racemic alcohols of the general formula II (Z=O) (having preferably R'=H, R" or R"'=aryl), in several cases a preferred reaction of one enantiomer is observed and thus optically enriched alcohols can be obtained.

During the transformation of a prochiral ZCR'R"R"'-rest of compounds of the general formula III into a chiral rest, in several cases an asymmetric induction is observed. Stereospecific reactions which may be used for this purpose are e.g. alkylation or aldolisation after deprotonation, Grignard reaction or reactions with organo-lithium compounds. During work-up favourable conditions for the synthesis of chiral compounds are created not only by the presence of the protective group, but also by the easy separation of diastereomeric compounds of the general formula III from each other. Thus even asymmetric reactions with not very high enantiomeric excess (EE) yield good results. This way of application is illustrated by the alkylation of mercaptoacetic acid and its esters (in general formula II: Z=S, R',R"=H, R"'=COOR).

The following examples illustrate the present invention, with examples 1 and 2 referring to the preparation of the new chiral optically active compounds, whereas examples 3 to 12 illustrate the use of the new compounds according to the invention. In all examples the compounds of the general formula I or V respectively, are represented by compounds of the general formula Ib or Vb respectively, which are the enantiomers rotating to the right with A,B,C=methyl, D=H and endo-cis fused lactol ring (E) with X: n=O and Y: $(CH_2)_n$, n=1 and 2. For these protective group rests the abbreviations MBF (n=1) and MBP (n=2) are chosen.

In all given examples compounds rotating to the right are used as starting material. The enantiomers rotating to the left, which have, of course, identical physical data, are obtained without any change of the process of reaction, when starting from compounds rotating to the left.

EXAMPLE 1

MBF-Protective Group Reagents (a) MBF-OH via Reduction

[2S-(2α,3aα,4α,7α,7aα)]-2,3,3a,4,5,6,7,7a-Octahydro-7,8,8-trimethyl-4,7-methanobenzofuran-2-ol (MBF-OH) (n=1, W=H):

To a solution of 11,6 g [3aS-(3aα,4α,7α,7aα)]-3a,4,5,6,7,7a-Hexahydro-7,8,8-trimethyl-4,7-methanobenzofuran-2(3H)-on in 50 ml anhydrous toluene, 55 ml of a 20% solution of diisobutylaluminiumhydride in n-hexane are added under stirring at −40° C. After 2 hours at −40° C. 80 ml ether and 30 ml water are added. 2N sodium hydroxide is added during the work-up procedure to dissolve the precipitate of aluminiumhydroxide, the organic layer is separated and the aqueous phase extracted with ether. The combined organic phase is washed with water, dried and evaporated. Yield: 11,5 g (98%) colourless oil, which crystallizes at temperatures below −5° C., bp. 120° C./0,005 mm (airbath). $^1$H-NMR (CDCl$_3$): δ=5,55–5,75 (dd, 1H), 4,40 (d, I=9 Hz, 1H); 4,0 (s, 1H, exchanged with D$_2$O); 2,7–3,2 (m, 1H); 1,1–2,1 (m, 7H); 1,00/0,93/0,88 (3s, 9H). Content of β(endo)-anomer ~7%. The educt can be prepared as follows:

[3aS-(3aα,4α,7α,7aα)]-3a,4,5,6,7,7a-Hexahydro-7,8,8-trimethyl-4,7-methanobenzofuran-2(3H)-one: To a solution of 51 g camphoracetic acid in 750 ml ethanol and 121 ml 2N sodium hydroxide 9,2 g of sodium borohydride are added at room temperature. After stirring at 50° C. for 16 hours, the reaction mixture is concentrated to a volume of 450 ml and diluted to 750 ml with water. It is acidified with 10% sulfuric acid, and extracted with petrolether/ether=9:1 several times. The organic phase is washed with diluted sulfuric acid, dried and evaporated. The residue is dissolved in petrolether/ether=9:1 and extracted with a half concentrated solution of sodium bicarbonate, to which 2,5 percent methanol are added. The organic phase is dried, evaporated and the residue recrystallized from petrolether/ether=9:1. Yield: 25,5 g (55%) colourless crystals, mp. 48°–50° C.

(b) [2R-(2α(2'R*,3'aS*,4'R*,7'R*,7'aS*),3aα,4α,7α,7aα)]-2,2'-Oxybis-[2,3,3a,4,5,6,7,7a-octahydro-7,8,8-trimethyl-4,7-methanobenzofuran] )MBF-O-MBF) (n=1, W=MBF):

(1) To a solution of 1 g MBF-OH in 5 ml ether 5 drops of ether saturated with hydrogen chloride are added and allowed to stand over molecular sieve 4 Å for 3 hours. The solution is decanted, the ether allowed to evaporate and the crystalline residue recrystallized from petrolether. Yield: 0,83 g (87%); colourless crystals, mp. 151°–152° C.; $[α]_D^{20}$=+193° (c=2,25 in THF). $^1$H-NMR (CDCl$_3$): δ=5,64/5,62/5,58/5,56 (dd, 1H); 4,25 (d, I=9,5 Hz, 1H); 2,7–3,15 (m, 1H); 1,0–2,1 (m, 7H); 0.98/0,90/0,87 (3s, 9H).

(2) To a solution of 1,05 g O-MBF-methanol in 5 ml ether 5 drops of ether saturated with hydrogen chloride are added and the reaction mixture is allowed to evaporate. The crystalline residue is recrystallized from petrolether. Yield 0,77 g (80%) colourless crystals, mp. 150°–152° C.

(c) [2S-(2α,3aα,4α,7α,7aα)]-2,3,3a,4,5,6,7,7a-Octahydro-2-methoxy-7,8,8-trimethyl-4,7-methanobenzofuran (O-MBF-Methanol) (n=1, W=CH$_3$): To a solution of 1,0 g MBF-OH and 0,33 g methanol in 20 ml ether/petrolether=1:1 about 10 mg p-toluenesulfonic acid and a few beads of molecular sieve 4 Å are added and the reaction mixture stirred for 1 hour at room temperature. The solution is diluted with ether and extracted with a solution of sodium hydrogencarbonate. The organic layer is dried and evaporated. Yield: 1,06 g (99%) colourless oil, bp. 80° C./0,02 mm (airbath). $^1$H-NMR (CDCl$_3$): δ=5,17/5,14/5,10/5,07 (dd, 1H); 4,2 (d, I=9 Hz, 1H); 3,3 (s, 3H); 2,7–3,1 (m, 1H); 1,1–2,2 (m, 7H); 0,97/0,91/0,88 (3s, 9H). Content of β/endo-anomer ~7%.

(d) [2S-(2α,3aα,4α,7α,7aα)]-2,3,3a,4,5,6,7,7a-Octahydro-2-ethoxy-7,8,8-trimethyl-4,7-methanobenzofuran (O-MBF-ethanol) (n=1, W=ethyl): Synthesis is achieved corcorresponding to (c) using ethanol: colourless oil bp. 90° C./0.02 mm (airbath). $^1$H-NMR (CDCl$_3$): δ=5,34/5,32/5,29/5,27 (dd, 1H); 4,27 (d, I=9,3 Hz; 1H); 3,45 (q, I=8 Hz, 2H); 2,7–3,1 (m, 1H); 1,4–1,9 (m, 8H); 1,1–1,25 (m, 3H); 0,97/0,90/0,86 (3s, 9H). Content of β/endo-anomer ~7%.

(e) [2S-(2α,3aα,4α,7α,7aα)]-2,3,3a,4,5,6,7,7a-Octahydro-2-isopropoxy-7,8,8-trimethyl-4,7-methanobenzofuran (O-MBF-Isopropanol) (n=1, W=CH(CH$_3$)$_2$): Synthesis is achieved corresponding to (c) using isopropanol: colourless oil bp. 90° C./0.02 mm (airbath). $^1$H-NMR (CDCl$_3$): δ=5.44/5.42/5.39/5.37 (dd, 1H); 4,26 (d, I=9,5 Hz; 1H); 3,7–4,2 (m, 1H); 2,5–3,0 (m, 1H); 1,0–1,9 (m, 13H); 0,97/0,90/0,85 (3s, 9H). Content of β/endo-anomer ~7%.

(f) [3aR-(3aα,4α,7α,7aα)]-3a,4,5,6,7,7a-Hexahydro-7,8,8-trimethyl-4,7-methanobenzofuran (V; Anhydro-MBF): A solution of 0,50 g MBF-OH in 5 ml thionylchloride is stirred for 2 hours at room temperature. Excess thionylchloride is evaporated in vacuo. The residue is taken up in 10 ml anhydrous ether and stirred with 1 ml triethylamine for 2 hours at 50° C. The reaction mixture is filtered, the ether evaporated in vacuo and the crude product cleaned by column chromatography (eluent:petrolether/ether=100:1, silicagel impregnated with triethylamine). Yield: 0.32 g (71%) anhydro-MBF; colourless oil; $^1$H-NMR (CDCl$_3$): δ=6,36/6,34/6,33/7,31 (dd, 1H); 4,72 (t, I=2,8 Hz, 1H); 4,67/4,65/4,54/4,52 (dd, 1H); 3,22–3,53 (m, 1H); 1,0–1,8 (m, 5H); 0,94/0,92/0,91 (3s, 9H).

EXAMPLE 2

MBP-Protective Group Reagents (a) MBP-OH-via reduction

[2S-(2α,4aα,5α,8α,8aα)]-3,4,4a,5,6,7,8,8a-Octahydro-8,9,9-trimethyl-5,8-methano-2H-1-benzopyran-2-ol (MBP-OH) (n=2, W=H): Synthesis corresponding to MBF-OH starting from [4aS-(4aα,5α,8α,8aα)]-3,4,4a,5,6,7,8,8a-octahydro-8,9,9-trimethyl-5,8-methano-2H-1-benzopyran-2-one yields colourless crystals, mp. 98°–101° C. $^1$H-NMR (CDCl$_3$): δ=5.35 (t, I=6 Hz, 1H); 3,95 (d, I=10 Hz, 1H); 3,5 (s, 1H); 2,35–1,0 (m, 10H); 0,90 (s, 6H); 0,86 (s, 3H).

(b) [2R-2α(2′R*,4a′S*,5′R*,8′R*,8a′S*),4aα,5α,8α,8aα]-2,2′-Oxybis[3,4,4a,5,6,7,8,8a-octahydro-8,9,9-trimethyl-5,8-methano-2H-1-benzopyran] (MBP-O-MBP) (n=2, W=MBP): Synthesis is achieved corresponding to MBF-O-MBF starting from MBP-OH; colourless crystals, mp. 123°–124° C.; $[\alpha]_D^{26} = +167°$ (c=2,0 in n-hexane); $^1$H-NMR (CDCl$_3$): δ=5,28 (t, I=6,5 Hz, 1H); 3,73 (d, I=9,5 Hz, 1H); 1,7–2,2 (m, 3H); 1,0–1,6 (m, 7H); 0,89 (s, 6H); 0,83 (s, 3H).

(c) [2S-(2α,4aα,5α,8α,8aα)]-3,4,4a,5,6,7,8,8a-Octahydro-2-methoxy-8,9,9-trimethyl-5,8-methano-2H-1-benzopyran (O-MBP-Methanol) (n=2, W=CH$_3$): Synthesis is achieved corresponding to MBF-O-methanol starting from MBP-OH. Colourless oil, bp. 80° C./0.02 Torr (air bath); $^1$H-NMR (CDCl$_3$): δ=4,77 (t, I=8 Hz, 1H); 3,71 (d, I=10 Hz; 1H); 3,32 (s, 3H); 1,13–2,25 (m, 10H); 0,90 (s, 6H); 0,87 (s, 3H).

EXAMPLE 3

Use as a Protective Group

Formation of acetal (general procedure): A 5% solution of MBF-OH, MBF-O-MBF, MBP-OH, MBP-O-MBP or anhydro-MBF and a compound II (1 to 1,4 equivalents) in anhydrous ether (or dichlormethane, THF, chloroform, petrolether/ether) is stirred at room temperature for 2 hours after addition of catalytic amounts of p-toluenesulfonic acid (or HCl saturated ether) and a few beads of molecular sieve 4 Å. Solid sodium bicarbonate and sodium sulphate are added. The reaction mixture is filtered and evaporated. If necessary the residue is fractioned by column chromatography using silica gel impregnated with triethylamine. Along this general procedure also the compounds used for resolution of racemates in the following examples are prepared.

Examples using nonchiral compounds II:

(a) [2S-(2α,3aα,4α,7α,7aα)]-[(2,3,3a,4,5,6,7,7a-Octahydro-7,8,8-trimethyl-4,7-methanobenzofuran-2-yl)oxy]acetonitrile (O-MBF-hydroxyacetonitrile) (Z=O, R′=R″=H, R′″=CN): Starting from 2,0 g MBF-O-MBF and 0.80 g hydroxyacetonitrile in dichlormethane catalyzed by p-toluenesulfonic acid 2.0 g (82%) colourless crystals are obtained after purification using column chromatography; mp. 33°–34° C.; $[\alpha]_D^{20} = +188°$ (in n-hexane); $^1$H-NMR (CDCl$_3$): δ=5,40 (d, I=4,5 Hz, 1H); 4,1–4,35 (m, 3H); 2,7–3,1 (m, 1H); 1,1–2,0 (m, 7H); 0,96/0,89/0,84 (3s, 9H).

(b) [2S-(2α,3aα,4α,7α,7aα)]-2,3,3a,4,5,6,7,7a-Octahydro-2-(cyclohexyloxy)-7,8,8-trimethyl-4,7-methanobenzofuran (O-MBF-Cyclohexanol) (Z=O, R′=H, R″R′″=—(CH$_2$)$_5$—): The compound is prepared following the general procedure; colourless oil, bp. 90° C./0,02 mm (air bath); $^1$H-NMR (CDCl$_3$): δ=5,49/5,47/5,44/5,42 (dd, 1H); 4,26 (d, I=9,4 Hz, 1H); 3,3–3,8 (m, 1H); 2,7–3,1 (m, 1H); 1,1–2,0 (m, 17H); 0,96/0,89/0,85 (3s, 9H).

(c) [2S-(2α,3aβ,4β,7β,7aβ)]-[(2,3,3a,4,5,6,7,7a-Octahydro-7,8,8-trimethyl-4,7-methanobenzofuran-2-yl)amino]acetic acid-t-butylester-chlorhydrate (N-MBF-Aminoacetic Acid-t-butylesterchlorhydrate) (Z=N⊕H$_2$Cl, R′=R″=H, R′″=COO-t-Bu): To a solution of 1,0 g MBF-OH (MBF-O-MBF and MBP-O-MBP do not react with amines) and 0,70 g aminoacetic acid-t-butylester in dichloromethane a few beads of molecular sieve 4 Å and catalytic amounts of p-toluenesulfonic acid are added. After 2 hours anhydrous ether saturated with hydrogen chloride is added to the decanted solution. The reaction mixture is evaporated in vacuo and the residue recrystallized from petroether/ether. Yield: 1,29 g (73%) colourless crystals, mp. 155° C.; $[\alpha]_D^{20} = +75°$ (c=1,2 in dichlormethane); $^1$H-NMR (CDCl$_3$): δ=9,87 (s, 2H); 5,28 (d, 1H); 4,53 (d, I=10 Hz, 1H); 3,72 (s, 2H); 3,13–3,44 (m, 1H); 2,32–2,72 (m, 2H); 1,0–1,78 (m, 14H); 0,99/0,90/0,84 (3s, 9H).

EXAMPLE 4

Resolution of racemic alcohols

This process consists of 3 steps: 1. Acetalformation, 2. Resolution of the diastereomers, 3. Cleavage of the protective group.

(a) Acetal formation of racemic 1-phenylethanol using the MBF-protective group: 1,0 g MBF-O-MBF and 2,61 g rac. 1-phenylethanol following the general procedure in example 3. Excess 1-phenylethanol is removed using coloumn chromatography (eluent: petrolether/ether 20:1). The yield of O-MBF-phenylethanol (mixture of diastereomers (R)/(S)∼2:1 according to $^1$H-NMR) is 1,14 g (88%) colourless oil bp. 120° C./0,005 mm (airbath). In the following separation of diastereomers using column chromatography over silica gel impregnated with triethylamine (eluent: petrolether/ether=20:1) 895 mg (56%) (R)-O-MBF-1-phenylethanol and 345 mg (22%) (S)-diastereomer are obtained. (R)-O-MBF-1-phenylethanol [2S-(2α(S*),3aα,4α,7α,7aα]-2,3,3a,4,5,6,7,7a-octahydro-7,8,8-trimethyl-2-(1-phenylethoxy)4,7-methanobenzofuran (Z=O, R′=phenyl, R″=H, R′″=CH$_3$): colourless crystals, mp. 72°–74° C. (petrolether); $[\alpha]_D^{21} = +221°$ (c=8,3 in benzene); $^1$H-NMR(CDCl$_3$): δ=7,25 (s; 5H); 5,12 (t, I=3 Hz; 1H); 4,78 (q, I=6,6 Hz; 1H); 4,32 (d, I=9,1 Hz; 1H); 2,7–3,1 (m, 1H); 1,0–1,8 (m, 10H) 0,95 (s; 3H); 0,86 (s; 6H). (S)-O-MBF-1-phenylethanol [(2S-2α(R*),3aα,4α,7α,7aα)]-2,3,3a,4,5,6,7,7a-octahydro-7,8,8-trimethyl-2-(1-phenylethoxy)-4,7-methanobenzofuran (Z=O, R′=H, R″=phenyl, R′″=CH$_3$); colourless oil $[\alpha]_D^{21} = +21,4°$ (c=12 in benzene); $^1$H-NMR (CDCL$_3$; δ=7,30 (s; 5H); 5,53/5,50/5,48/5,45 (dd; 1H); 4.73 (q, I=6,5 Hz; 1H); 3,95 (d, I=9 Hz; 1H); 2,7–3,1 (m; 1H); 1,0–2,0 (m; 10H); 0,88 (s; 6H); 0,72 (s; 3H).

(b) Resolution of racemic 1-phenylethanol using anhydro-MBF (V): following the procedure given in (3) 1,00 g anhydro-MBF and 2,74 g rac. 1-phenylethanol yield 1,48 g (88%) O-MBF-1-phenylethanol; (mixture of diastereomers) ratio of diastereomers as given in example (4a), which is fractioned using column chromatography as indicated in example (4a).

Cleaving of the Protective Group:

General procedure for methanolysis: To 1 mmol of acetal in 10 ml methanol catalytic amounts of p-toluenesulfonic acid are added and the reaction mixture is allowed to rest for 3 hours. 0,5 g of solid sodium hydrogen carbonate and sodium sulphate are added, it is filtered, evaporated and the residue fractioned using column chromatography. At first O-MBF-methanol is eluted, which reacts to yield MBF-O-MBF again following the procedure given in example (1). Next the chiral alcohol is eluted.

(R)-1-phenylethanol (II: Z=O, R′=phenyl, R″=E, R′″=CH$_3$): Out of 308 mg (R)-O-MBF-1-phenylethanol (eluent: petrolether/ether=100:1, then ether) 88 mg (72%) (R)-1-phenylethanol are obtained. Colourless oil, bp. 100° C./12 mm (airbath). $[\alpha]_D^{23} = +52,4°$ (c=3,72 in benzene).

(S)-1-phenylethanol (II: Z=O, R'=H, R—=phenyl, R'''=CH$_3$): Out of 299 mg (S)-O-MBF-1-phenylethanol (eluent: petrolether/ether 20:1, then ether) 105 mg (86%) (S)-1-phenylethanol are obtained. Colourless oil, bp. 100° C./12 mm (airbath). $[\alpha]_D^{20} = = -46,2°$ (c=2,5 in chloroform).

(c) Resolution of racemic 1-phenylethanol using the MBP-protective group: Acetal formation: The reaction product is obtained out of 0,77 g MBP-O-MBP and 0,93 rac. 1-phenylethanol following the general procedure given in example (3). After removal of excess 1-phenylethanol using column chromatography (eluent: petrolether/ether=20:1) 1,07 g (90%) O-MBP-1-phenylethanol (mixture of diastereomers (R)/(S)~2:1 according to $^1$H-NMR) are obtained. Colourless oil.

In the separation step corresponding to O-MBF-1-phenylethanol 0,66 g (55%) (R)-O-MBP-1-phenylethanol and 0,34 g (29%) (S)-O-MBP-1-phenylethanol are obtained.

(R)-O-MBP-1-phenylethanol ([2S-(2α(S*),4aα,5α,-8α,8aα)]-3,4,4a,5,6,7,8,8a-octahydro-8,9,9-trimethyl-2(1-phenylethoxy)-5,8-methano-2H-1-benzopyran) (Z=O, R'=phenyl, R''=H, R'''==CH$_3$): colourless oil, bp. 125° C./0.001 mm (airbath). $[\alpha]_D^{23} = = +188°$ (c=2,25 in n-hexane); $^1$H-NMR (CDCl$_3$): δ=7,29 (s; 5H); 4,81 (m; 2H); 3,84 (d, I=10 Hz; 1H), 1,6–2,3 (m; 3H); 1,0–1,6 (m: 10H); 0,92 (s: 3H); 0.90 (s; 6H).

(S)-O-MBP-1-phenylethanol([2S-(2α(R*),4aα,5α,-8α,8aα)]-3,4,4a,5,6,7,8,8a-octahydro-8,9,9-trimethyl-2(1-phenylethoxy)-5,8-methano-2H-1-benzopyran) (Z=O, R'=H, R''=phenyl, R'''==CH$_3$): colourless crystals, mp. 85°–86° C., $[\alpha]_D^{22} = +52°$ (c=0,50 in n-hexane); $^1$H-NMR(CDCl$_3$): δ=7,30 (s; 5H); 5,16 (t; 1H); 4,75 (q; 1h; 3,56 (d, I=10 Hz; 1H); 1,6–2,3 (m: 3H); 1,0–1,6 (m: 10H); 0,82/0,78/0,47 (3s; 9H). Cleaving of the protective group is achieved by using methanolysis along the general procedure given in example (4b) for O-MBF-1-phenylethanol.

(d) Resolution of racemic 1-phenylpropanol using the MBF-protective group: Acetalformation: The reaction product is obtained out of 1,0 g MBF-OH and 2,75 g rac. 1-phenylpropanol following the general procedure in example (3). Excess 1-phenylpropanol is removed using column chromatography (eluent: petrolether/ether=10:1). The yield of the mixture of diastereomers ((R)/(S)~3,5:1 according to $^1$H-NMR) is 1,36 g (85%).

Separation: In the following separation of diastereomers using column chromatography over silica gel impregnated with triethylamine (eluent: petrolether/ether=20:1) 974 mg (61%) (R)-O-MBF-1-phenylpropanol and 249 mg (16%) (S)-O-MBF-1-phenylpropanol are obtained.

(R)-O-MBF-1-phenylpropanol([2S-(2α(S*),3aα,4α,-7α,7aα)]-2,3,3a,4,5,6,7,7a-octahydro-7,8,8-trimethyl-2-(1-phenylpropoxy)-4,7-methanobenzofuran) (Z=O, R'=phenyl, R''=H, R'''=ethyl): colourless oil, bp. 100° C./0,01 mm (airbath); $[\alpha]_D^{20} = +176°$ (c==1,9 in n-hexane); $^1$H-NMR(CDCl$_3$): δ=7,23 (s; 5H); 5,10 (t, I=3 Hz; 1H); 4,5 (t, I=6,5 Hz; 1H); 4,3 (d, I=9 Hz; 1H); 2,3–3,2 (m; 1H); 1,0–1,9 (m; 9H); 1,0 (s; 3H); 0,9 (s; 6H); 0,88 (t, I=6,5 Hz; 3H).

(S)-O-MBF-1-phenylpropanol([2S-(2α(R*),3aα,4α,-7α,7aα)]-2,3,3a,4,5,6,7,7a-octahydro-7,8,8-trimethyl-2-(1-phenylpropoxy)-4,7-methanobenzofuran) (Z=O, R'=H, R''=phenyl, R'''=ethyl): colourless crystals, mp. 50°–54° C. (petrolether); $[\alpha]_D^{20} = +72,7°$ (c=0,8 in hexane); $^1$H-NMR(CDCl$_3$): δ=7,23 (s; 5H); 5,42 (t, I=3 Hz; 1H); 4,40 (t, I=6 Hz; 1H); 3,78 (d, I=9 Hz; 1H); 2,6–3,1 (m; 1H) 1,1–1,9 (m; 9H); 0,7–1,0 (m; 9H); 0,64 (s; 3H). Cleaving of the protective group is achieved using methanolysis following the general procedure given in example (4b).

(R)-1-phenylpropanol (II: Z=O, R'=phenyl, R''=H, R'''==ethyl): Out of 551 mg (R)-O-MBF-1-phenylpropanol (column chromatography (eluent: petrolether/ether=5:1, then ether) 199 mg (83%) (R)-1-phenylpropanol are obtained as colourless oil. $[\alpha]_D^{20} = +41,7°$ (c=2,3 in n-hexane).

(S)-1-phenylpropanol (II: Z=O, R'=H, R''=phenyl, R'''==ethyl): Out of 65,7 mg (S)-O-MBF-1-phenylpropanol (column chromatography (eluent: petrolether/ether=5:1, then ether) 21 mg (74%) (S)-1-phenylpropanol are obtained as colourless oil. $[\alpha]_D^{20} = -33,1°$ (c=0,4 in THF).

(e) Resolution of racemic 2-methyl-1-phenylpropanol using the MBF-protective group: Acetalformation: The product is obtained out of 2,0 g MBF-OH and 5,6 g rac. 2-methyl-1-phenylpropanol following the general procedure as shown in example 3. After removal of excess 2-methyl-1-phenylpropanol using column chromatography (eluent: petrolether/ether=20:1) 2,65 g (89%) O-MBF-2-methyl-1-phenylpropanol (mixture of diastereomers (R)/(S)~2:1 according to $^1$H-NMR) are obtained. Colourless oil, bp. 110° C./0,001 mm (airbath).

Separation: Using column chromatography as given in example (4a) yields 1,51 g (R)-O-MBF-2-methyl-1-phenylpropanol and 0,85 g (29%) (S)-O-MBF-2-methyl-1-phenylpropanol.

(R)-O-MBF-2-methyl-1-phenylpropanol([2S-(2α(S*),3aα,4α,7α,7aα)]-2,3,3a,4,5,6,7,7a-octahydro-7,8,8-trimethyl-2-(2-methyl-1-phenylpropoxy)-4,7-methanobenzofuran) (Z=O, R'=phenyl, R''=H, R'''=isopropyl): colourless oil, bp. 100° C./0,01 mm (airbath); $[\alpha]_D^{20} = +157°$ (c=1,2 in n-hexane); $^1$H-NMR(CDCl$_3$): δ=7,27 (s; 5H); 5,08 (t, I=2,8 Hz; 1H); 4,30 (d, I=9,8 Hz; 1H); 4,26 (d, I=7,3 Hz; 1H); 2,8–3,1 (m; 1H); 1,1–2,0 (m; 8H); 1,0 (s; 3H); 0,98/0,72 (2d, I=7,3 Hz; 6H); 0,93 (s; 6H).

(S)-O-MBF-2-methyl-1-phenylpropanol([2S-(2α(R*),3aα,4α,7α,7aα)]-2,3,3a,4,5,6,7,7a-octahydro-7,8,8-trimethyl-2-(2-methyl-1-phenylpropoxy)-4,7-methanobenzofuran) (Z=O, R'=H, R''=phenyl, R'''=isopropyl): colourless oil, bp. 100° C./0,01 mm (airbath); $[\alpha]_D^{20} = +70°$ (c=0,9 in n-hexane; $^1$H-NMR(CDCl$_3$): δ=7,25 (s; 5H); 5,4 (t, I=2,8 Hz); 4,07 (d, I=7,4 Hz; 1H); 3,61 (d, I=9,5 Hz; 1H); 2,7–3,0 (m; 1H); 1,1–2,0 (m; 8H); 0,94/0,72 (2d, I=7,4 Hz; 6H); 0,82 (s; 6H); 0,58 (s, 3H).

(f) Resolution of racemic 1-(3-bromophenyl)ethanol using the MBP-protective group: Acetalformation: The product is obtained out of 1,00 g MBP-OH and 1,44 g rac. 1-(3-bromophenyl)ethanol following the general procedure given in example (3). Separation: Column chromatography of the crude product as shown in example (4a) (eluent: petrolether/ether=100:1) yields—apart from excess 1-(3-bromophenyl)ethanol—820 mg (45%) (R)-O-MBP-1-(3-bromophenyl)ethanol and 610 mg (34%) (S)-O-MBP-1-(3-bromophenyl)ethanol.

(R)-O-MBP-1-(3-bromophenyl)ethanol([2S-(2α(S*)-,4aα,5α,8α,8aα)]-3,4,4a,5,6,7,8,8a-octahydro-8,9,9-trimethyl-2-[1-(3-bromophenyl)]ethoxy-5,8-methano-2H-1-benzopyran) (Z=O, R'=mBrC$_6$H$_4$, R''=H, R'''=CH$_3$): colourless oil; $^1$H-NMR(CDCl$_3$):

δ=7,1–7,5 (m; 4H); 4,63–4,92 (m; 2H); 3,84 (d, I=10 Hz; 1H); 1,0–2,25 (m; 13H); 0,93 (s; 3H); 0,90 (s; 6H).

(S)-O-MBP-1-(3-bromophenyl)ethanol ([2S(2α(R*)-,4a,5α,8α,8aα)-3,4,4a,5,6,7,8,8a-octahydro-8,9,9-trimethyl-1(3-bromophenyl)ethoxy]-5,8-methano-2H-1-benzopyran) (Z=O, R'=H, R''=mBrC₆H₄, R'''=CH₃): colourless crystals; mp. 88°–90° C. ¹H-NMR(CDCl₃): δ==7,1–7,5 (m; 4H); 5,11 (t, I=7 Hz; 1H); 4,68 (q, I=6,5 Hz; 1H); 3,45 (d, I=10 Hz; 1H); 0,80–2,28 (m; 13H); 0,75 (s; 6H); 0,34 (s; 3H).

Cleaving of the protective group is achieved by using methanolysis following the general procedure shown in example (4b).

(g) Resolution of racemic 1-tetralol using the MBP-protective group: Acetalformation: 1,0 g MBP and 1,16 g rac. 1-tetralol following the general procedure shown in example (3). Removal of excess 1-tetralol using column chromatography yields 1,54 g (95%) O-MBP-1-tetralol (mixture of diastereomers), colourless oil.

Separation: Column chromatography (eluent: petrolether/ether==80:1) as shown in example (4a) yields 0,77 g (48%) (R)-O-MBP-1-tetralol and 0,75 g (46%) (S)-O-MBP-1-tetralol.

(R)-O-MBP-1-tetralol([2S-(2α(S*),4aα,5α,8α,8aα)]-3,4,4a,5,6,7,8,8a-octahydro-8,9,9-trimethyl-2-[1-(1,2,3,4-tetrahydronaphthyl)oxy]-5,8-methano-2H-1-benzopyran) (Z=O, R'R'''=C₆H₄—(CH₂)₃, R''=H): colourless oil, bp. 130° C./0,01 mm (airbath); [α]_D^{20}==+79° (c=0,54 in dichlormethane) ¹H-NMR(CDCl₃): δ=6,9–7,3 (m; 4H); 5,19 (t, I=7 Hz; 1H); 4,63 (t, I=6 Hz; 1H); 3,86 (d, I=9 Hz; 1H); 2,6–2,8 (m; 2H); 1,0.2,3 (m; 14H); 0,90 (s; 9H).

(S)-O-MBP-1-tetralol([2S(2α(R*),4aα,5α,8α,8aα)]-3,4,4a,5,6,7,8,8a-octahydro-8,9,9-trimethyl-2-[1-(1,2,3,4-tetrahydronaphthyl)oxy]-5,8-methano-2H-benzopyran) (Z=O, R'=H, R''R'''=C₆H₄—(CH₂)₃): colourless oil, b.p. 130° C./0,01 mm (airbath); [α]_D^{20}==+40° (c=0,54 in dichloromethane) ¹H-NMR(CDCl₃): δ=6,9–7,3 (m; 4H); 5,13 (t, I=7 Hz; 1H); 2,6–2,8 (m; 2H); 1,0–2,3 (m; 14H); 0,99 (s; 3H); 0,92 (s; 6H).

Methanolysis following the general procedure as shown in example (4b) yields:

(R)-1-tetralol (II: Z=O, R'R'''=C₆H₄-(CH₂)₃, R''=H): Out of 70 mg (R)-O,MBP-1-tetralol 24 mg (79%) (R)-1-tetralol are obtained: colourless oil, [α]_D^{20}= −23° (c=0,48 in chloroform).

(S)-1-tetralol (II: Z=O, R'=H, R''R'''=C₆H₄-(CH₂)₃): Out of 59 mg (S)-O-MBP-1-tetralol 25 mg (97%) (S)-1-tetralol are obtained: colourless oil, [α]_D^{20}= +24° (c=0,50 in chloroform).

(h) Resolution of racemic 1,2-diphenyl-1,2-ethandiol using the MBF-protective group: Acetalformation: 1,67 g MBF-OH and 2,20 g rac. 1,2-diphenyl-1,2-ethandiol following the general procedure as shown in example 3).

Separation: Column chromatography (eluent: petrolether/ether==10:1 yields 0,89 g (27%) (R)-O-MBF-1,2-ethandiol and 1,77 g (53%) (S)-O-MBF-1,2-diphenyl-1,2-ethandiol.

(R)-O-MBF-1,2-diphenyl-1,2-ethandiol([2R-(2α(R*,R*),3aα,4α,7α,7aα)]-1,2-diphenyl-1-[(2,3,3a,4,5,6,7,7a-octahydro-7,8,8-trimethyl-4,7-methanobenzofuran-2-yl)oxy]ethanol) (Z=O, R'=H, R''==phenyl, R'''=CHOH-Ph): colourless crystals, mp. 72°–74° C. (petrolether): [α]_D^{20}= +113,2° (c=0,92 in dichloromethane) ¹H-NMR (CDCl₃): δ=7,14 (s; 10H); 5,45 (t, I=3 Hz; 1H); 4,72/4,64/4,50/4,42 (dd; 2H); 3,65 (d, I=9,5 Hz; 1H); 3,29 (s; 1H); 2,6–3,1 (m; 1H); 0,9–1,9 (m; 7H); 0,84 (s; 6H); 0,53 (s; 3H).

(S)-O-MBF-1,2-diphenyl-1,2-ethandiol([2R-(2α(S*,S*),3aα,4α,7α,7aα)]-1,2-diphenyl-1-[(2,3,3a,4,5,6,7,7a-octahydro-7,8,8-trimethyl-4,7-methanobenzofuran-2-yl)oxy]ethanol) (Z=O, R'=phenyl, R''=H, R'''=CHOH-Ph): colourless oil, [α]_D^{20}= +104,7° (c==1,27 in ether); ¹H-NMR(CDCl₃): δ=7,13 (s; 10H); 5,16 (t, I=3 Hz; 1H); 4,66 (s; 2H); 3,92 (d, I=9,5 Hz; 1H); 3,52 (br. s; 1H); 2,6–3,1 (m; 1H); 1,0–1,9 (m; 7H); 0,91/0,87/0,81 (3s; 9H).

EXAMPLE 5

Resolution of racemic thiols (a) Resolution of racemic 1-phenylethanthiol using the NBF-protective group: Acetalformation: Out of 500 mg MBF-O-MBF and 450 mg rac. 1-phenylethanol following the general procedure as shown in example 3). The crude product obtained is separated using column chromatography over silica gel impregnated with triethylamine (eluent: first petrolether/ether=100:1, then 50:1). Yield: 311 mg (37%) (R)-S-MBF-1-phenylethanthiol, 297 mg (35%) (S)-S-MBF-1-phenylethanthiol.

(R)-S-MBF-1-phenylethanthiol([2R-(2α(R*),3aα,4α,7α,7aα)]-2,3,3a,4,5,6,7,7a-octahydro-7,8,8-trimethyl-2-[(1-phenylethyl)thio]-4,7-methanobenzofuran) (Z=S, R'=phenyl, R''=H, R'''=CH₃): colourless oil; [α]_D^{20}= +445° (c=0,9 in n-hexane); ¹H-NMR (CDCl₃): δ=7,2–7,4 (m; 5H); 5,19/5,14/5,11/5,06 (dd: 1H); 4,40 (d, I=9 HZ, 1H); 4,16 (q, I=7,5 Hz; 1H) 2,65–3,05 (m; 1H); 1,00–2,25 (m; 10H); 0,95 (s; 3H); 0,88 (s; 6H).

(S)-S-MBF-1-phenylethanthiol([2R-(2α(S*),3aα,4α,7α,7aα)]-2,3,3a,4,5,6,7,7a-octahydro-7,8,8-trimethyl-2-[(1-phenylethyl)thiol]-4,7-methanobenzofuran) (Z=S, R'=H, R''=phenyl, R'''=CH₃): colourless oil; [α]_D^{20}= +144° (c=1,6 in n-hexane; ¹H-NMR (CDCl₃): δ=7,2 (m; 5H); 5,68/5,64/5,61/5,57 (dd; 1H); 4,28 (d, I=9,8 Hz; 1H); 4,15 (q, I=7 Hz; 1H); 2,6–3,0 (m; 1H); 1,0–2,3 (m; 10H); 0,90/0,87/0,81 (3s; 9H).

A solution of 59,5 mg (S)-S-MBF-1-phenylethanthiol (8% content of (R)-diastereomer according to ¹H-NMR) in 10 ml methanol is kept at 45° C. for 15 hours after addition of a catalytic amount of p-toluenesulfonicacid. An aqueous solution of sodium hydrogencarbonate and petrolether are added, the aqueous phase extracted with petrolether and the combined organic phases dried, evaporated and chromatographed using petrolether as eluent: 21,3 mg (82%) (S)-1-phenylethanthiol (II: Z=S, R'=H, R''=phenyl, R'''=CH₃): colourless oil; [α]_D^{20}= −52,8° (c=0,3 in THF).

(b) Resolution of racemic 1-phenylethanthiol using the MBP-protective group: Acetalformation: Out of 1,20 g MBP-OH and 0,79 rac. 1-phenylethanthiol following the general procedure as shown in example 3).

The crude reaction product is separated using column chromatography over non impregnated silicagel (eluent: petrolether/ether=100:1; yield: 0,85 g (45%) (R)-S-MBP-1-phenylethanthiol, 0,83 g (44%) (S)-S-MBP-1-phenylethanthiol.

(R)-S-MBP-1-phenylethanthiol([2R-(2α(R*),4aα,5α,8α,8aα)]-3,4,4a,5,6,7,8,8a-octahydro-8,9,9-trimethyl-2-[(1-phenylethyl)thio]-5,8-methano-2H-1-benzopyran) (Z=S, R'=phenyl, R''=H, R'''=CH₃): colourless oil, bp. 120° C./0,01 mm (airbath); [α]_D^{20}==+382° (c=0,90 in dichlormethane); ¹H-NMR(CDCl₃):

δ=7,15–7,35 (m; 5H); 4,91 (t, I=9 Hz; 1H); 4,06 (q, I=8 Hz 1H); 3,99 (d, I=10 Hz; 1H); 1,0–2,2 (m; 13H); 0,95 (s; 3H); 0,92 (s; 6H).

(S)-S-MBP-1-phenylethanthiol([2R-(2α(S*),4aα,5α,-8α,8aα)]-3,4,4a,5,6,7,8,8a-octahydro-8,9,9-trimethyl-2-[(1-phenylethyl)thio]-5,8-methano-2H-1-benzopyran) (Z=S, R″=phenyl, R′=H, R‴=CH$_3$): colourless oil, bp. 120° C./0,01 mm (airbath); [α]$_D^{20}$==+129° (c=0,61 in dichlormethane); $^1$H-NMR(CDCl$_3$): δ=7,1–7,3 (m: 5H); 5,37 (t, I=8 Hz; 1H); 4,09 (q, I=7 Hz; 1H); 3,93 (d, I=10 Hz; 1H); 1,0–2,25 (m; 13H); 0,89 (s; 6H); 0,81 (s; 3H).

Cleaving of the protective group:

(R)-1-phenylethanthiol (II: Z=S, R′=phenyl, R″=H, R‴==CH$_3$): A solution of 68 mg (R)-S-MBP-1-phenylethanthiol in 10 ml methanol refluxed for 10 hours after addition of a catalytic amount of p-toluenesulfonic acid. Ether is added, then solid bicarbonate and sodium sulphate. The reaction mixture is filtered, evaporated and chromatographed (eluent: petrolether/ether=100:1). Yield: 20,3 mg (71%) (R)-1-phenylethanthiol; [α]$_D^{20}$=+98° (c=0,41 in tetrachloromethane).

(S)-1-phenylethanthiol (II: Z=S, R′=H, R″=phenyl, R‴==CH$_3$): Out of 70 mg (S)-S-MBP-1-phenylethanthiol 20,5 mg (70%) (S)-1-phenylethanthiol are obtained. [α]$_D^{20}$=−90° (c=0,41 in chloroform).

EXAMPLE 6

Resolution of racemic amines

Resolution of racemic 1-phenylethanamine: A solution of 970 mg MBF-OH (MBF-O-MBF does not react) and 446 mg rac. 1-phenylethanamin in 25 ml petrolether/ether=1:1, is stirred for 12 hours at room temperature after addition of catalytic amounts of p-toluenesulfonic acid. Then solid sodium hydrogenecarbonate and sodium sulfate are added, the reaction mixture is filtered and evaporated, the residue taken up in anhydrous ether, ethereal hydrochloric acid is added and the reaction mixture evaporated again to dryness at 40° C. in vacuo.

The residue is dissolved in as little dichloromethane as possible, the double amount of anhydrous THF is added, and the solution concentrated at 40° C. in vacuo to a quarter of its original volume and allowed to crystallize at −20° C. Yield: 490 mg (40%).

(S)-N-MBF-1-phenylethanamine-chlorohydrate (contaminated with 10% (R)-diastereomer according to $^1$H-NMR). The colourless crystals are purified by recrystallization from dichloromethane/THF.

[2R-(2α(S*),3aβ,4β,7β,7aβ)]-2,3,3a,4,5,6,7,7a-octahydro-7,8,8-trimethyl-N-(1-phenylethyl)-4,7-methano-2-benzofuranamine, chlorohydrate (Z=N$^+$H$_2$Cl, R′=H, R″=phenyl, R‴=CH$_3$); mp. 175°–180° C. (decomp., subl. at 150° C./0,01 mm (airbath) without decomp.); [α]$_D^{20}$=+34,1° (c=0,9 in dichloromethane); $^1$H-NMR(CDCl$_3$): δ==10,0 (br. s; 1H); 9,7 (br. s; 1H); 7,2–7,7 (m; 5H); 5,0 (br. s; 1H); 4,4 (d, I=9,3 Hz; 1H); 4,2 (br. s; 1H); 2,9–3,4 (m; 1H); 1,0–2,3 (m; 10H); 0,93/0,85/0,76 (3s; 9H). The mother liquor obtained during the preparation of (S)-M-MBF-1-phenylethanaminchlorhydrate is evaporated, triturated with ether, taken up in a small amount of dichloromethane, diluted with ether and allowed to crystallize. 613 mg (50%) colourless crystals are obtained (contaminated with 28% (S)-diastereomer according to $^1$H-NMR). Further recristallisation from dichloromethane/ether yields pure.

(R)-N-MBF-1-phenylethanamine chlorohydrate([2R-(2α(R*),3aβ,4β,7β,7aβ)]-2,3,3a,4,5,6,7,7a-octahydro-7,8,8-trimethyl-N-(1-phenylethyl)-4,7-methano-2-benzofuranamine, chlorohydrate) (Z=N$^+$H$_2$Cl, R′=phenyl, R″=H, R‴=CH$_3$): colourless crystals, mp. 212°–215° C.; [α]$_D^{20}$=+76,4° (c=1,6 in dichloromethane); $^1$H-NMR (CDCl$_3$): δ=9,76 (br. s; 1H); 7,2–7,7 (m; 5H); 4,63 (d, I==8,5 Hz; 1H); 4,4 (br. s; 2H); 2,8–3,5 (m; 1H); 1,1–2,6 (m; 10H); 1,02 (s; 3H); 0,89 (s; 6H).

Cleaving: 317 mg (S)-N-MBF-1-phenylethanamine in 30 ml ether are stirred ten times with each 5 ml of 10% aqueous citric acid for 15 minutes. The aqueous phases are washed with ether, combined, neutralized with solid sodium carbonate and thoroughly extracted with ether. The ether-phase is extracted with 10% acetic acid and the acidic aqueous phase neutralized with sodium carbonate. It is extracted with ether, dried and evaporated. Yield: 107 mg (83%).

(S)-1-phenylethanamine (II: Z=NH, R′=H, R″=phenyl, R‴=CH$_3$).

EXAMPLE 7

Separation of diastereomeric Acetals obtained from Cyanohydrins

Formation of acetal: Starting from 1,0 g MBF-OH and 0,73 g rac.-α-hydroxybenzeneacetonitrile following the general procedure given in example 3; reaction time: 1 hour. Working-up is effected by washing with aqueous sodium bicarbonate and sodium bisulfite solutions. 1,55 g (97%) O-MBF-hydroxybenzeneacetonitrile (mixture of diastereomers (R)/(S)~1:1 according to $^1$H-NMR) is separated into the following fractions using column chromatography (eluent: petrolether/ether=20:1) over silicagel impregnated with triethylamine: 691 mg (43%) (R)-OMBF-α-hydroxybenzeneacetonitrile, 309 mg (19%) mixture of diastereomers and 483 mg (30%) (S)-O-MBF-α-hydroxybenzeneacetonitrile.

(S)-O-MBF-α-hydroxybenzeneacetonitrile ([2R-(2α(S*),3aα,4α,7α,7aα)]-α-[(2,3,3a,4,5,6,7,7a-octahydro-7,8,8-trimethyl-4,7-methanobenzofuran-2-yl)oxy]-benzeneacetonitrile) (Z=O, R′=phenyl, R″=H, R‴=CN): colourless crystals, mp. 83°–86° C. (petrolether); $^1$H-NMR (CDCl$_3$): δ=7,3–7,6 (s; 5H); 5,3–5,45 (m; 2H); 4,51 (d, I=9 Hz; 1H); 2,8–3,3 (m; 1H); 1,0–2,3 (m; 7H); 1,00 (s; 3H); 0,92 (s; 6H).

(R)-O-MBF-α-hydroxybenzeneacetonitrile ([2R-(2α(R*),3aα,4α,7α,7aα)]-α-[(2,3,3a,4,5,6,7,7a-octahydro-7,8,8-trimethyl-4,7-methanobenzofuran-2-yl)oxy]-benzeneacetonitrile) (Z=O, R′=H, R″=phenyl, R‴=CN): colourless crystals, p. 67°–70° C. (petrolether); [α]$_D^{20}$=+120° (c=7,0 in THF); $^1$H-NMR (CDCl$_3$): δ=7,3–7,6 (s; 5H); 5,71 (d, I=4,6 Hz; 1H); 5,51 (s; 1H); 4,23 (d, I=9,3 Hz; 1H); 2,65–3,1 (m; 1H); 1,05–2,2 (m; 7H); 0,92 (s; 6H); 0,88 (s; 3H).

EXAMPLE 8

Preparation of optically active Imidoesterchlorohydrates via methanolysis of protected cyanohydrins and if desired hydrolysis to yield optically active esters:

(S)-α-hydroxybenzeneethanimidoacid methylester chlorohydrate (II: Z=O, R′=phenyl, R″=H, R‴=C(OCH$_3$)N$^+$H$_2$Cl$^−$): To a solution of 204 mg (S)-O-MBF-α-hydroxybenzeneacetonitrile in 3 ml anhydrous ether 2 ml anhydrous ethereal hydrochloric acid are added and allowed to rest at 5° C. for 17 hours.

The precipitate is filtered and dried in vacuo at 40° C. Yield: 23,2 mg (93%) colourless hygroscopic crystals, mp. 84°–87° C. (decomp.). Evaporation of the mother liquor and recrystallisation from petrolether yields 101 mg (80%) MBF-O-MBF.

(S)-α-hydroxybenzeneacetic acid methylester ((S)-mandelic acid methylester) (II: Z=O, R'=phenyl, R''=H, R'''=COOCH₃): To a solution of 105 mg (S)-α-hydroxybenzeneethanimidoacid methylester chlrohydrate in 10 ml 0,2N hydrochloric acid ether is added and the mixture stirred for 3 hours. The ethereal layer is separated, the aqueous phase extracted twice with ether, the combined organic phase washed with an aqueous solution of sodium bicarbonate, dried and evaporated. The yield is 75,1 mg (87%) colourless crystals, mp. 54°–55° C.; $[\alpha]_D^{20} = +168°$ (c=1,36 in benzene).

(R)-α-hydroxybenzeneethanimidoacid methylester chlorohydrate (II: Z=O, R'H, R''=phenyl, R'''=C(OCH₃)N+H₂Cl−): Out of 199 mg (R)-O-MBF-α-hydroxyacetonitrile 96,9 mg (75%) colourless hygroscopic crystals are obtained following the procedure given for the (S)-enantiomer. Mp. 84°–87° C. (decomp.)

(R)-α-hydroxybenzeneacetic acid methylester ((R)-mandelic acid methylester) (II: Z=O, R'=H, R''=phenyl, R'''=COOCH₃): From 61 mg (R)-α-hydroxybenzeneethanimidoacid methylesterchlorohydrate, as described for the (S)-enantiomer: Yield: 41,7 mg (84%) colourless crystals, mp. 54°–55° C.; $[\alpha]_D^{20} = -176°$ (c=0,83 in benzene).

Example 9

Preparation of optically enriched Alcohols via Enantioselective Acetal Formation (a) 1-Phenylethanol from a mixture of diastereomers obtained through enantioselective formation of acetals starting from rac.-1-phenylethanol:

Starting from 421 mg O-MBF-1-phenylethanol (mixture of diastereomers (R)/(S)~2:1 according to ¹H-NMR; prepared as described in example 4(a)) 149 mg (87%) 1-phenylethanol are obtained as a colourless oil after cleavage of the protective group via methanolysis following the general procedure given in example 4(b)). $[\alpha]_D^{20} = +20,3°$ (c=2,1 in chloroform).

(b) Optically active 1,2-diphenyl-2-hydroxyethanone from a mixture of diastereomers obtained through enantioselective acetal formation starting from rac. 1,2-diphenyl-2-hydroxyethanone: Formation of the acetal: 2,078 g MBF-O-MBF and 9,145 g rac.-1,2-diphenyl-2-hydroxyethanone are allowed to react following the general procedure given in example 3. O-MBF-1,2-diphenyl-2-hydroxyethanone (mixture of diastereomers (R)/(S)~3:7) is freed from excess 1,2-diphenyl-2-hydroxyethanone by trituration with a small amount of dichloromethane, followed by column filtration (eluent: petrolether/ether=30:1). The resulting O-MBF-1,2-diphenyl-2-hydroxyethanone is dissolved in 6 ml methanol, 10 mg p-toluenesulfonic acid are added, the precipitate formed is filtered and washed with petrolether. Yield: 1,83 g (78%) 1,2-diphenyl-2-hydroxyethanone, $[\alpha]_D^{26} = +45,0°$ (c=0,52 in chloroform).

Asymmetric Induction: The following reaction scheme explains the reactions described in the following examples:

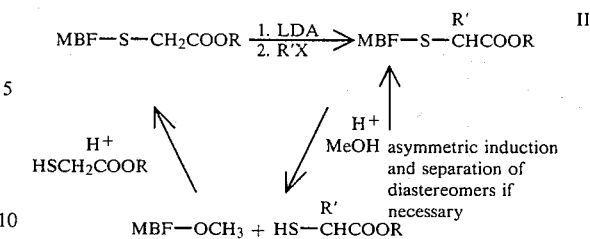

EXAMPLE 10

Asymmetric Methylation of Mercaptoacetic acid Formation of acetal:

S-MBF-mercaptoacetic acid ([2R-(2α,3aα,4α,7α,7aα)]-[(2,3,3a,4,5,6,7,7a-octahydro-7,8,8-trimethyl-4,7-methanobenzofuran-2-yl)thio]-acetic acid) (Z=S, R'=R''=H, R'''=COOH): To a solution of 376 mg O-MBF-methanol and 214 mg mercaptoacetic acid in 5 ml dichloromethane 3 drops of ether saturated with hydrogen chloride are added. After 3 hours resting the reaction mixture is poured into a mixture of ether and 2N potassium hydroxide and the organic layer is extracted several times with 2N potassium hydroxide. The alkaline phases are acidified with semi-concentrated hydrochloric acid at 0° C. and extracted with dichloromethane. The dichloromethane phase is washed with dilute hydrochloric acid, dried, evaporated and excess mercaptoacetic acid removed at 50° C./1 mm; yield: 430 mg colourless oil, bp. 120° C./0,001 mm (airbath); ¹H-NMR (CDCl₃): δ=5,80/5,78/5,72/7,70 (dd; 1H); 4,36 (d, I=9,5 Hz; 1H); 2,7–3,75 (m; 3H); 1,0–2,4 (m; 7H); 0,97/0,90/0,84 (3s; 9H).

Formation of acetal can also be effected with MBF-OH, MBP-OH MBF-O-MBF or MBR-O-MBP following this procedure using ether saturated with hydrogen chloride as a catalyst, with mercaptoacetic acid being removed in vacuo at 50° C./1 mm.

Methylation: To a solution of 2,45 ml diisopropylamine in 10 ml anhydrous THF 7,8 ml of a 1,6N solution of n-butyllithium in n-hexane is added at −30° C. under nitrogen. After 45 minutes it is cooled to −75° C. and 1,12 g S-MBF-mercaptoacetic acid in anhydrous THF is added dropwise. After 45 minutes at −75° C. 400 μl iodomethane is added. The reaction mixture is kept at −75° C. for 1 hour, then at −60° C. for 1 hour and then allowed to reach −10° C. within 2 hours. Ether and dilute sodium hydroxide are added. The organic phase is extracted several times with aqueous sodium hydroxide, the combined alkaline phases washed with petrolether and acidified with semi-concentrated hydrochloric acid under cooling with ice. It is extracted with dichloromethane, washed with a small amount of hydrochloric acid, dried and evaporated. Yield: 1,05 g (89%) (R)-S-MBF-2-mercaptopropanoic acid ([2R-(2α(R*),3aα,4α,7α,7aα)]-2-[(2,3,3a,4,5,6,7,7a-octahydro-7,8,8-trimethyl-4,7-methanobenzofuran-2-yl)thio]propanoic acid) (Z=S, R'=H, R''=CH₃, R'''=COOH): colourless oil, bp. 145° C./0.001 mm (airbath); 1H-NMR (CDCl₃): δ=9,7 (s; 1H); 5,90/5,86/5,79 (dd; 1H); 4,4 (d, I=9,5 Hz; 1H); 3,65 (q, I=7 Hz, 1H); 2,7–3,1 (m; 1H); 1,1–2,4 (m; 10H); 0,99/0,92/0,88 (3s; 9 Hz). The following deferring signals are attributed to the (S)-diastereomer: 5,83/5,79/5,75/5,71 (dd); 4,44 (d, I=9,5 Hz); 3,6 (q, I=7 Hz); 0,85 (s). A content of ~23% of (S)-diastereomer is estimated from the integral.

Cleavage of the protective group accompanied by simultaneous formation of the ester: 260 mg S-MBF-mercaptopropanoic acid ((R)/(S)~3:1) are dissolved in 30 ml dichloromethane and 20 ml methanol and refluxed for 17 hours under nitrogen after addition of 0,1 ml concentrated sulfuric acid. The reaction mixture is neutralized with a saturated solution of sodium hydrogencarbonate the organic layer is separated and the aqueous phase extracted with ether. The combined organic phase is dried and the solvent removed by careful distillation at slightly reduced pressure. After distillation at 80° C./30 mm (airbath) 100 mg (91%) 2-mercaptopropanoic acid methylester are obtained. (In the residue remain 190 mg (99%) O-MBF-methanol.) Colourless oil. Optical rotation of the acid (after hydrolysis): $[\alpha]_D^{20} = +26,8°$ (c=1,2 in chloroform).

EXAMPLE 11

Asymmetric Induction: Alkylation followed by separation of diastereomers (a) Separation of diastereomers of S-MBF-2-mercaptopropanoic acid from the asymmetric methylation (example 10) after formation of the ester:

Formation of the ester: a solution of 579 mg of crude product of the methylation of S-MBF-mercaptoacetic acid in 20 ml ether is treated with several portions of an ethereal solution of diazomethane until a yellow colour remains and evolution of nitrogen ceases. The reaction mixture is washed with an aqueous solution of sodium carbonate and 0,5N hydrochloric acid, dried and evaporated. The crude product obtained (560 mg; 94%) is chromatographed over silicagel impregnated with triethylamine. The following product containing fractions are obtained: 170 mg mixture of diastereomers ((R)/(S)=2:3), 114 mg mixture of diastereomers ((R)/(S)=78:22) and 270 mg pure (R)-S-MBF-2-mercaptopropanoic acid methylester ([2R-(2α(R*),3aα,4α,-7α,7aα)]-2-[(2,3,3a,4,5,6,7,7a-octahydro-7,8,8-trimethyl-4,7-methanobenzofuran-2-yl)thio]propanoic acid methylester) (Z=S, R'=H, R''=CH$_3$, R'''=COOCH$_3$): colourless oil, bp. 110° C./0,01 mm (airbath); $[\alpha]_D^{20} = +373°$ (c=1,26 in n-hexane); $^1$H-NMR (CDCl$_3$): δ=5,83/5,80/5,75/7,72 (dd; 1H); 4,36 (d, I=9,5 Hz; 1H); 3,74 (s; 3H); 3,63 (q, I=7 Hz; 1H); 2,7-3,2 (m; 1H); 1,1-2,5 (m; 10H); 0,98/0,92/0,89 (3s; 9H).

(b) Asymmetric ethylation with subsequent separation of diastereomers:

To a solution of 2,23 ml diisopropylamine in 10 ml anhydrous THF 7,12 ml of a 1,6N solution of n-butyllithium in n-hexane are added at −30° C. under nitrogen. After 30 minutes 2 ml anhydrous HMPA are added. The reaction mixture is cooled to −75° C. and 1,03 g S-MBF-mercaptoacetic acid in 5 ml anhydrous THF are added. After 45 minutes at −75° C. 1 ml iodoethane is added and the reaction mixture kept at −35° C. for 1 hour and then at −15° C. for 4 hours. Work-up proceeds along the procedure given in example 10. Yield: 1,11 g (97%) (R)-S-MBF-2-Mercaptobutanoic acid ([2R-(2α(R*),3aα,4α,7aα)]-2-[(2,3,3a,4,5,6,7,7a-octahydro-7,8,8-trimethyl-4,7-methanobenzofuran-2-yl)thio]-butanoic acid) (Z=S, R'=H, R''=ethyl, R'''=COOH): colourless oil, bp. 145° C./0,03 mm (airbath); $^1$H-NMR (CDCl$_3$): δ=5,78/5,75/5,71/5,68 (dd; 1H); 4,33 (d, I=9,5 Hz; 1H); 3,39 (t; 1H); 2,7-3,2 (m; 1H); 1,1-2,4 (m; 9H); 1,02 (t, I=7 Hz; 3H); 0,97/0,91/0,87 (3s; 9H). The following deferring signals are attributed to the (S)-diastereomer: 3,36 (t); 0,84 (s). Integration enables an estimation of a 20% content of (S)-diastereomer.

Formation of the ester: 660 mg of the reaction product of the ethylation of S-MBF-mercaptoacetic acid are treated following the procedure given in example 11(a). The product obtained (620 mg; 90%) is separated by column chromatography using silicagel impregnated with triethylamine (eluent: petrolether/ether=20:1). The following product containing fractions were obtained: 162 mg mixture of diastereomers and 315 mg (R)-S-MBF-2-mercaptobutanoic acid methylester (content of (S)-diastereomer≦3%) ([2R-(2α(R*),3aα,4α,-7α,7aα)]-2-[(2,3,3a,4,5,6,7,7a-octahydro-7,8,8-trimethyl-4,7-methanobenzofuran-2-yl)thio]butanoic acid methylester) (Z=S, R'=H, R''=ethyl, R'''=COOCH$_3$): colourless oil, bp. 115° C./0,03 mm (airbath); $[\alpha]_D^{20} = +356°$ (c=2,9 in n-hexane); $^1$H-NMR (CDCl$_3$): δ=5,76/5,73/5,68/5,65 (dd; 1H); 4,33 (d, I=9,5 Hz; 1H); 3,73 (s; 3H); 3,4 (t, I=7 Hz; 1H); 2,7-3,2 (m; 1H); 1,1-2,35 (m; 9H); 0,98 (t; 3H); 0,98/0,92/0,87 (3s; 9H).

Cleavage of the protective group with simultaneous formation of the ester: From 168 mg (R)-S-MBF-2-mercaptobutanoic acid methylester following the procedure given in example 10). After distillation at 100° C./15 mm (airbath) 61 mg (81%) (R)-mercaptobutanoic acid methylester are obtained. Colourless oil; optical rotation of the corresponding acid (after hydrolysis) $[\alpha]_D^{20} = +29°$ (c=0,14 in ether).

c. Asymmetric methylation of mercaptoacetic acid methylester and separation of diasteromers:

Formation of acetal: From 3,6 g MBF-OH and 2,14 g mercaptoacetic acid methylester following the general procedure given in example 3; catalyst: 6 drops of ether saturated with hydrogen chloride. Column chromatography (eluent: petrolether/ether=10:1) yields 4,7 g (90%) colourless oil. S-MBF-mercaptoacetic acid methylester ([2R-(2α,3aα,4α,7α,7aα)]-[(2,3,3a,4,5,6,7,7a-octahydro-7,8,8-trimethyl-4,7-methanobenzopyran-2-yl)thio]acetic acid methylester) (Z=S, R'=R''=H, R'''=COOCH$_3$): bp. 105° C./0,001 mm (airbath); $^1$H-NMR (CDCl$_3$): δ=5,77/5,74/5,70/5,67 (dd; 1H); 4,33 (d, I=9,5 Hz; 1H); 3,74 (s; 3H); 2,7-3,03 (m; 1H); AB-signal (δ$_A$=3,20, δ$_B$=3,36, I=13,8 Hz; 2H); 1,0-2,4 (m; 7H); 0,97/0,90/0,84 (3s; 9H).

Methylation: To a solution of 1,53 ml diisopropylamine in 5 ml anhydrous THF 4,9 ml of a 1,6N solution of n-butyllithium in n-hexane are added under nitrogen at −50° C. After 20 minutes 3 ml HMPA are added and after another 10 minutes the reaction mixture is cooled to −75° C. and 1,01 g S-MBF-mercaptoacetic acid methylester in 5 ml anhydrous THF are added. After 40 minutes at −80° C. 0,36 ml iodomethane are added, the temperature is kept at −80° C. for 2 hours, then the reaction mixture is allowed to reach −40° C. and after 30 minutes at this temperature ether and aqueous sodium bicarbonate are added. The aqueous phase is extracted with ether, the combined organic phase is washed with 0,1N hydrochloric acid and water, dried and evaporated. Yield: 1,0 g (92%) colourless oil. Using coloumn chromatograpgy as described for the identical product in example 11(a) 0,55 g (51%) (R)-S-MBF-2-mercaptopropanoic acid methylester are isolated.

Figure 2:
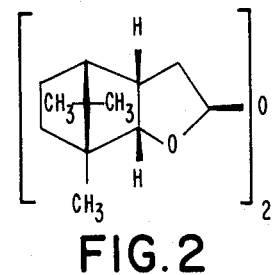
Figure 3:
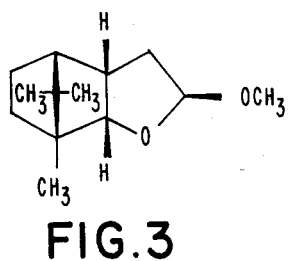
Figure 4:
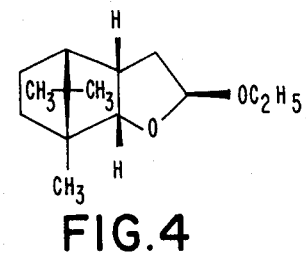
Figure 5:
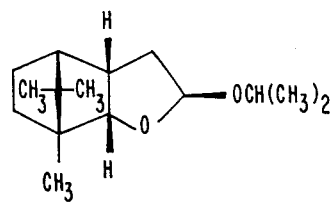
Figure 6:
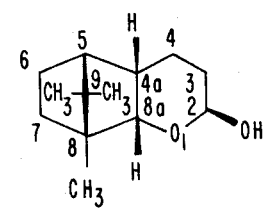
Figure 7:
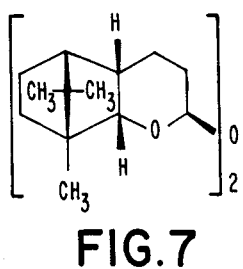
Figure 8:
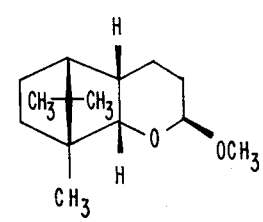
Figure 9:
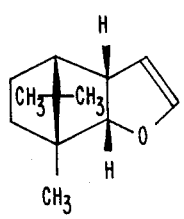
Figure 10:
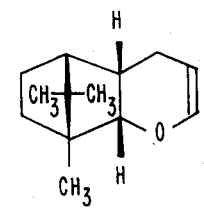

The compounds of Examples 1(a) to 1(e), 2(a) to 2(c), 1(f) and the anhydro compound of Example 2(a) are depicted in FIGS. 1–10, respectively.

What is claimed is:

1. Chiral, optically active (R)-enantiomer or (S)-enantiomer of the general formula

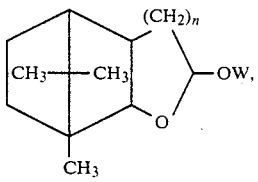
(Ia)

wherein W represents H, alkyl, cycloalkyl or

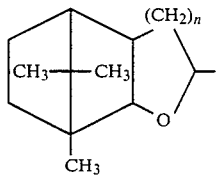

and n = 1 or 2, or the anhydro compound of the general formula

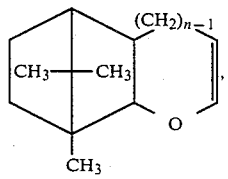
(Va)

wherein n has the same meaning as in the hydrated form of formula Ia.

2. Chiral, optically active (R)-enantiomer or (S)-enantiomer of the general formula

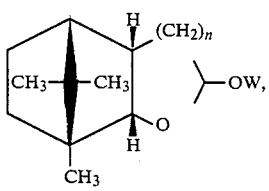
(Ib)

wherein W represents H, alkyl, cycloalkyl, or

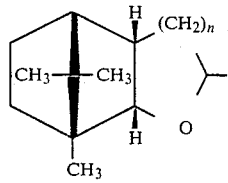

and n is 1 or 2, or the anhydro compound of the general formula

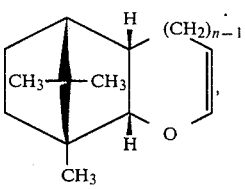
(Vb)

wherein n has the same meaning as in the hydrated form of formula Ib.

3. A compound according to claim 2 having the name (4aα,5α,8α,8aα)-4a,5,6,7,8,8a-hexahydro-8,9,9-trimethyl-4H-5,8-methanobenzopyran (R)- or (S)-enantiomer.

4. A compound according to claim 2 having the name (2α,3aα,4α,7α,7aα)-2,3,3a,4,5,6,7,7a-octahydro-7,8,8-trimethyl-4,7-methanobenzofuran-2-ol (R)- or (S)-enantiomer.

5. A compound according to claim 2 having the name (2α(2'R*,3'aS*,4'R*,7'R*,7aS*),3aα,4α,7α,7aα)-2,2'-oxybis[2,3,3a,4,5,6,7,7a-octahydro-7,8,8-trimethyl-4,7-methanobenzofuran] (R)- or (S)-enantiomer.

6. A compound according to claim 2 having the name (2α,3aα,4α,7α,7aα)-2,3,3a,4,5,6,7,7a-octahydro-2-methoxy-7,8,8-trimethyl-4,7-methanobenzofuran (R)- or (S)-enantiomer.

7. A compound according to claim 2 having the name (2α,3aα,4α,7α,7aα)-2,3,3a,4,5,6,7,7a-octahydro-2-ethoxy-7,8,8-trimethyl-4,7-methanobenzofuran (R)- or (S)-enantiomer.

8. A compound according to claim 2 having the name (2α,3aα,4α,7α,7aα)-2,3,3a,4,5,6,7,7a-octahydro-2-isopropoxy-7,8,8-trimethyl-4,7-methanobenzofuran (R)- or (S)-enantiomer.

9. A compound according to claim 2 having the name (2α,4aα,5α,8α,8aα)-3,4,4a,5,6,7,8,8a-octahydro-8,9,9-trimethyl-2H-5,8-methano-1-benzopyran-2-ol (R)- or (S)-enantiomer.

10. A compound according to claim 2 having the name (2α(2'R*,4'aS*,5'R*,8'R*,8'aS*),4aα,5α,8α,8aα)-2,2'-oxybis[3,4,4a,5,6,7,8,8a-octahydro-8,9,9-trimethyl-2H-5,8-methano-1-benzopyran] (R)- or (S)-enantiomer.

11. A compound according to claim 2 having the name (2α,4aα,5α,8α,8aα)-3,4,4a,5,6,7,8,8a-octahydro-2-methoxy-8,9,9-trimethyl-2H-5,8-methano-1-benzopyran (R)- or (S)-enantiomer.

12. A compound according to claim 2 having the name (3aα,4α,7α,7aα)-3a,4,5,6,7,7a-hexahydro-7,8,8-trimethyl-4,7-methanobenzofuran (R)- or (S)-enantiomer.

* * * * *